United States Patent [19]
Baumann et al.

[11] Patent Number: 6,026,511
[45] Date of Patent: Feb. 22, 2000

[54] PROTECTIVE ARTICLE HAVING A TRANSPARENT SHIELD

[75] Inventors: Nicholas R. Baumann, St. Paul; Shannon L. Dowdell Browne, Indianapolis; Michael P. Moulsoff, St. Paul; Jane K. Peterson, Eagan; Nicole V. McCullough, St. Paul, all of Minn.

[73] Assignee: 3M Innovative Properties Company, St. Paul, Minn.

[21] Appl. No.: 08/986,052

[22] Filed: Dec. 5, 1997

[51] Int. Cl.⁷ .................................................. A62B 18/00
[52] U.S. Cl. ........................... 2/9; 128/201.17; 128/206.19
[58] Field of Search ............................... 2/9, 11, 15, 206; 128/201.15, 201.17, 206.12, 206.13, 206.19, 206.23, 857, 858, 863

[56] References Cited

U.S. PATENT DOCUMENTS

| | | | |
|---|---|---|---|
| 366,697 | 1/1887 | Drummond | D24/110.2 |
| 911,476 | 2/1909 | Cheesman. | |
| 2,056,753 | 10/1936 | Wagner | 128/141 |
| 2,462,005 | 9/1949 | Schauweker | 128/146 |
| 2,762,368 | 1/1956 | Bloomfield | 128/146 |
| 3,276,034 | 10/1966 | Cupp | 2/8 |
| 4,296,746 | 10/1981 | Mason, Jr. et al. | 128/201.15 |
| 4,701,965 | 10/1987 | Landis | 2/428 |
| 4,807,619 | 2/1989 | Dyrud et al. | 128/206.16 |
| 4,816,333 | 3/1989 | Lange et al. | 428/331 |
| 4,825,878 | 5/1989 | Kuntz et al. | 128/857 |
| 4,867,178 | 9/1989 | Smith | 128/858 |
| 4,944,294 | 7/1990 | Borek, Jr. | 128/206.19 |
| 4,945,574 | 8/1990 | Dagher | 2/9 |
| 4,965,887 | 10/1990 | Paoluccio et al. | 2/9 |
| 5,020,533 | 6/1991 | Hubbard et al. | 128/206.23 |
| 5,067,174 | 11/1991 | Ritchey et al. | 2/10 |
| 5,138,714 | 8/1992 | Smith | 2/9 |
| 5,150,703 | 9/1992 | Hubbard et al. | 128/206.12 |
| 5,307,796 | 5/1994 | Kronzer et al. | 128/206.16 |
| 5,383,450 | 1/1995 | Hubbard et al. | 128/206.23 |
| 5,406,943 | 4/1995 | Hubbard et al. | 128/206.12 |
| 5,406,944 | 4/1995 | Gazzara | 128/206.19 |
| 5,446,925 | 9/1995 | Baker et al. | 2/9 |
| 5,553,608 | 9/1996 | Reese et al. | 128/206.24 |
| 5,584,078 | 12/1996 | Saboory | 2/427 |
| 5,585,186 | 12/1996 | Scholz et al. | 428/412 |
| 5,765,556 | 6/1998 | Brunson | 128/206.19 |
| 5,813,398 | 9/1998 | Baird et al. | 128/201.17 |

FOREIGN PATENT DOCUMENTS

| | | |
|---|---|---|
| 0 625 344 A2 | 11/1994 | European Pat. Off. . |
| 0 650 712 A1 | 5/1995 | European Pat. Off. . |
| 3800959 | 8/1988 | Germany . |
| 8107939 | 4/1996 | Japan . |
| 2 304 054 | 3/1997 | United Kingdom . |
| WO 89/10106 | 11/1989 | WIPO . |
| WO 96/18691 | 6/1996 | WIPO . |
| WO 96/28216 | 9/1996 | WIPO . |
| WO 96/28217 | 9/1996 | WIPO . |
| WO 97/23571 | 7/1997 | WIPO . |

*Primary Examiner*—Michael A. Neas
*Attorney, Agent, or Firm*—James A. Rogers

[57] ABSTRACT

A shield that is configured for use with a mask to form a protective article. The mask includes (i) a central portion having a pair of opposed edges, (ii) a first portion joined to an edge of the central portion, and (iii) a second portion joined to the other edge of the central portion. At least one of the central, upper and lower portions is formed from filter media. The shield is flexible and transparent, having upper and lower edges, with the lower edge having at least one projection. It is dimensioned to cover the portion of the wearer's face not covered by the mask. The shield is adapted to be attached to the mask and moved between a first position in which the shield lower edge and the lower edge projection lies in front of the mask central portion, and a second position in which the lower edge projection engages the mask such that at least a portion of the shield lower edge lies behind the central portion.

15 Claims, 6 Drawing Sheets

PROTECTIVE ARTICLE HAVING A TRANSPARENT SHIELD

The invention relates to protective articles having a transparent shield attached to a mask.

BACKGROUND OF THE INVENTION

Face masks generally fall into two categories. The first category includes loose-fitting masks designed to protect a patient from infectious particles expelled by the wearer. The second category includes tight-fitting masks, also know as respirators, that are designed to protect the wearer from inhaling particles or toxins in the ambient air by passing inhaled air through a filter. In a medical environment, respirators also protect patients from particles expelled by the wearer.

It is also desirable to protect the wearer's face (and, in particular, the wearer's eyes) from droplets, sprays, or splashes of body liquids such as blood and saliva encountered during surgery, in the emergency room, or in areas with patients in droplet isolation. Masks combined with transparent plastic sheets have been used for this purpose.

SUMMARY OF THE INVENTION

In one aspect, the invention features a protective article that includes a shield and a mask. The mask includes (i) a central portion having a pair of opposed edges, (ii) a first portion joined to an edge of the central portion, and (iii) a second portion joined to the other edge of the central portion. At least one of the central, upper, and lower portions is formed from filter media. The shield is flexible and transparent, having upper and lower edges, with the lower edge having at least one projection. It is dimensioned to cover the portion of the wearer's face not covered by the mask. The shield is adapted to be attached to the mask and moved between a first position in which the shield lower edge and the lower edge projection lies in front of the mask central portion, and a second position in which the lower edge projection engages the mask such that at least a portion of the shield lower edge lies behind the central portion.

In preferred embodiments, the upper and lower edges of the shield are substantially arcuate. The shield lower edge may also include a plurality of projections. In one preferred embodiment, the shield lower edge includes a centrally located, arcuately shaped cut-out portion intermediate a pair of projections.

The shield is preferably attached to the mask at the outside corners of the shield lower edge. In one preferred embodiment, the shield is removably attached to the mask at one of the outside corners, while in another the shield is removably attached at both of the outside corners.

The mask may be in the form of a respirator. It may also include a nose clip. The shield preferably includes an anti-fogging, anti-reflective coating, e.g., a coating containing inorganic metal oxide particles. The shield and/or the mask may include an anti-glare strip, and the shield may be adapted for attachment to the wearer's head.

In a second aspect, the invention features another protective article that includes the above-described mask and a shield configured for use with the mask. The shield is flexible and transparent, having upper and lower edges, and is dimensioned to cover the portion of the wearer's face not covered by the mask. The shield is adapted to be moved between a first position in which the shield lower edge lies in front of the mask central portion, and a second position in which at least a portion of the shield lower edge lies behind the central portion.

The invention provides protective articles, featuring a mask and a shield adapted for use with the mask, where the user can adjust the shield to occupy a number of different positions relative to the mask. Thus, when worn, the shield can be positioned such that it bends and conforms to the wearer's face, thereby affording good protection from liquid splashes, including protection of the sides of the wearer's face. The shield's conformability also makes it comfortable to wear. When the protective article is not being worn, the shield can simply be moved to a different position to allow it to lay flat when the mask is also folded flat. The protective article is thus easily stored and shipped.

In the case of respirators, shields that are removable at one or more attachment points allow the wearer to fit the respirator to his/her face without interference from the shield, thereby ensuring a good fit. The wearer can also perform a "fit check" each time the wearer dons the respirator, also without interference from the shield. The wearer can then attach the shield and position it appropriately for best fit and coverage.

By removably attaching the shield to the mask, it can be removed when not needed. In addition, if the shield is damaged, the wearer can discard the damaged shield and readily attach another shield to the same mask portion, instead of having to discard the entire construction (i.e., mask plus shield).

Other features and advantages of the invention will be apparent from the following description of the preferred embodiments thereof, and from the claims.

DESCRIPTION OF THE PREFERRED EMBODIMENTS

Figure 1:
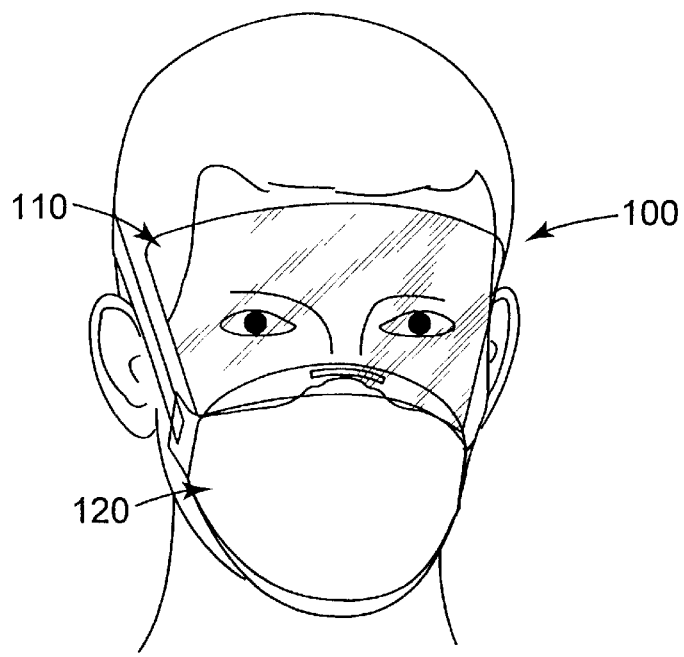
FIG. 1 is a perspective view of a protective article embodying the invention shown worn by a user.

Referring to FIGS. 1–4, a protective article 100 has a shield 110 and a mask 120. Shield 110 is flexible and transparent, covering the portion of the wearer's face not covered by mask 120, including the sides of the face. The shield 110 protects the wearer's eyes and skin from contact by potentially harmful liquids.

Suitable materials for shield 110 include polyester (e.g., polyethylene terephthalate, polybutylene terephthalate), polycarbonate, alkyldiglycolcarbonate, polyacrylates (e.g., polymethylmethacrylate), polystyrene, polysulfone, polyethersulfone, cellulose acetate butyrate, and the like, including blends and laminates thereof. Typically, shield 110 is provided in the form of a film or sheet. The shield is preferably provided with an anti-fogging, anti-reflective coating, e.g., containing inorganic metal oxide particles such as silica particles. Examples of suitable coating compositions, and methods for applying such compositions, are described, e.g., in (a) Scholz et al., U.S. Pat. No. 5,585,186 entitled "Coating Composition Having Anti-Reflective and Anti-Fogging Properties"; (b) Lange et al., U.S. Pat. No. 4,816,333 entitled "Silica Coating"; (c) Scholz et al., International Publication Number WO 96/18691 entitled "Coating Composition Having Anti-Reflective and Anti-Fogging Properties"; and (d) Scholz et al., International Publication No. WO 97/23571 entitled "Coating Composition Having Anti-Reflective and Anti-Fogging Properties," each of which is incorporated by reference. In addition, the shield, the mask, or both, may include a dark strip to reduce glare.

Mask 120 includes a central portion 126, an upper portion 128, and a lower portion 130, at least one of which is formed from filter media. The upper 128 and lower 130 portions are bonded to the central portion 126 at upper 127 and lower 129 edges, respectively. The upper portion 128 includes a nose clip 136 to aid in forming the mask 120 to the contours of the wearer's face. The outside corners of the shield's lower edge 112 and 114 are attached to the front of the mask 120 at the mask's attachment points 122 and 124. Attachment means for attaching the mask 120 to a wearer's head, such as elastic straps 132 and 134, or ear loops (not shown), attach to the mask at these attachment points 122 and 124. Alternately, the shield 110 may attach to the wearer's head in place of, or in addition to, the mask's attachment means.

Figure 5:
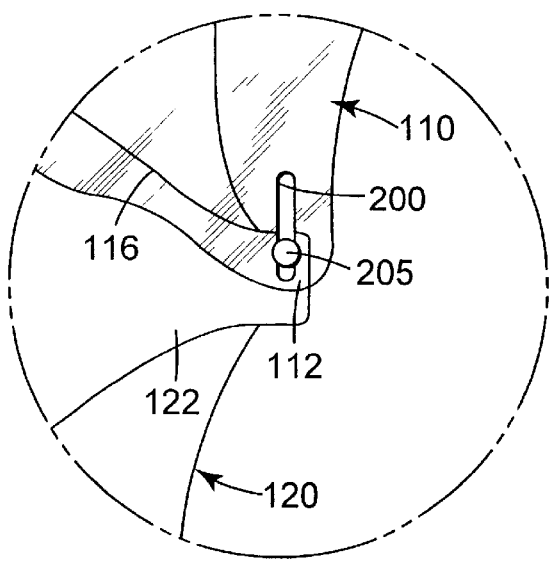
FIG. 5 is a detailed view of an alternate shield attachment device on the protective article of FIG. 1.

Shield 110 may be either permanently or removably attached to mask 120, although removable attachment is preferred. In addition, attachment may be the same at both ends, or different. Permanent attachment methods include ultra-sonic welding, adhesives, thermal bonding, staples, rivets, or stitching. Examples of suitable removable attachment methods include hook-and-loop type fasteners, snaps, or repositionable adhesives. FIG. 5 is a detailed view of another shield attachment method that could be either permanent or removable. The shield 110 includes a slot 200 located in an outside corner 112 of the shield lower edge 116. The mask 120 includes a peg 205 positioned at the mask attachment point 122. Shield slot 200 fits over mask peg 205, thereby allowing the shield 110 to move up and down with respect to mask 120. This slot and peg configuration can be permanent, or the shield slot 200 can snap onto, and off of, the mask peg 205, allowing the shield 110 to be removable. Other shield attachment methods and locations are also contemplated.

Figure 2:
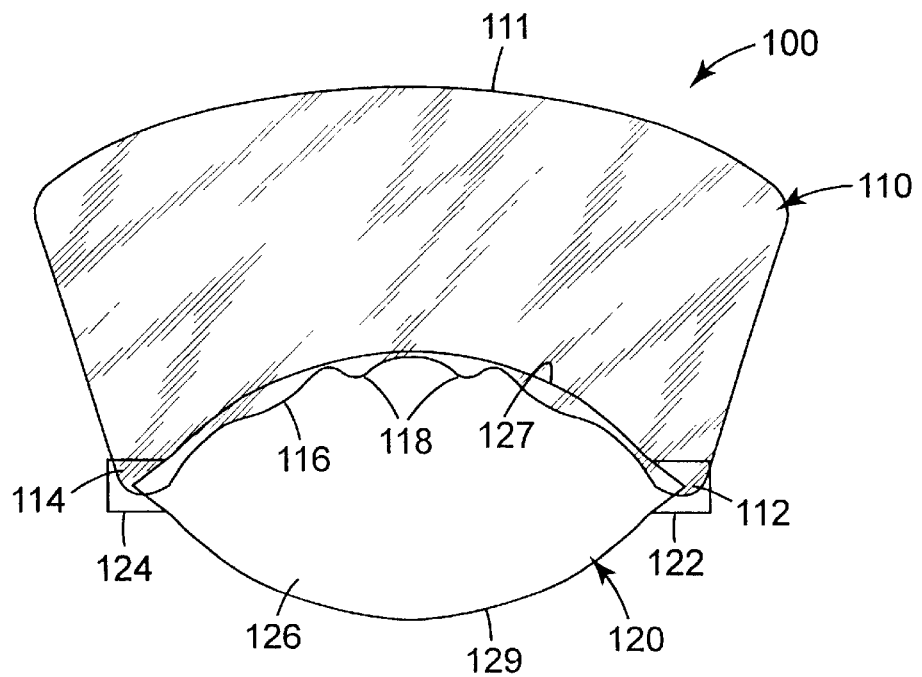
FIG. 2 is front view of the protective article of FIG. 1 in flat-fold configuration.
Figure 3:
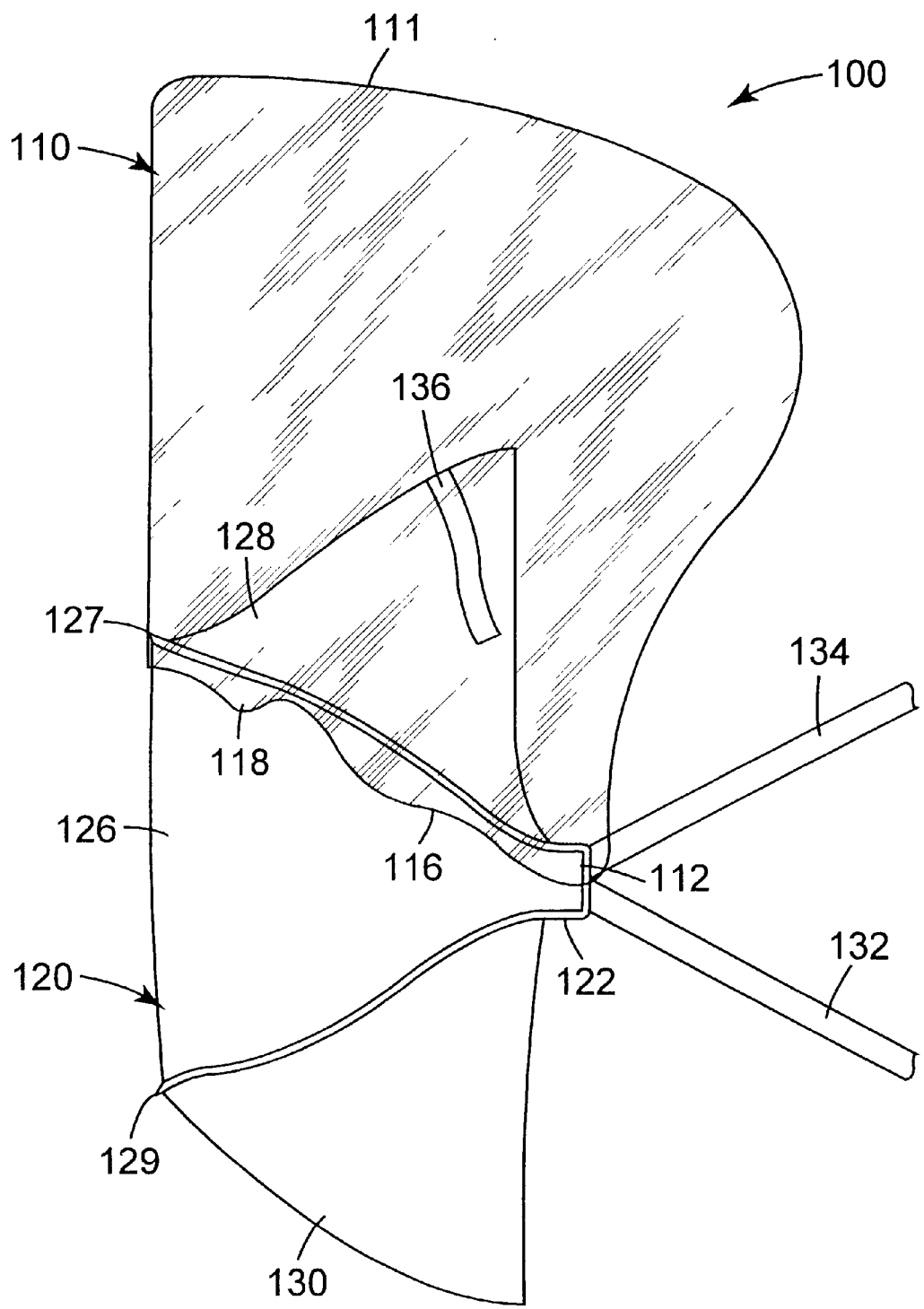
FIG. 3 is a side view of the protective article of FIG. 1 shown in an open, ready-to-use configuration with a shield in a first position.
Figure 4:
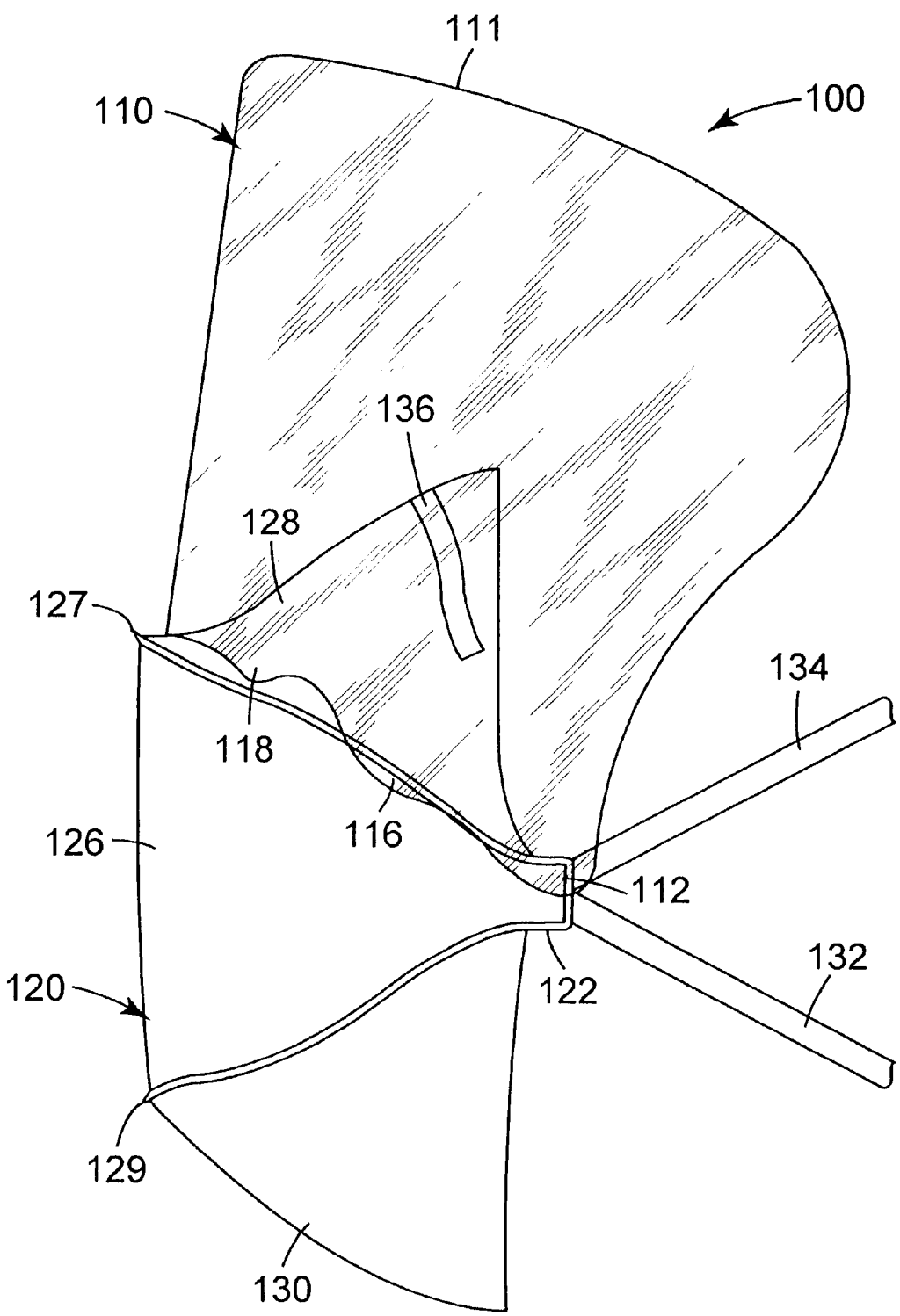
FIG. 4 is a side view of the protective article of FIG. 1 shown in an open, ready-to-use configuration with the shield in a second position.

Protective article 100 is shown in a flat folded configuration in FIG. 2. The shield 110 has substantially arcuate upper 111 and lower 116 edges, with a shape that approximates a circular ring sector with rounded corners. The substantially arcuate upper 111 and lower 116 edges of the shield 110 facilitate creaseless curvature of the shield 110 about the wearer's face when the protective article 100 is worn by a wearer, as shown in FIGS. 3 and 4, thus ensuring clear visibility during use. In the flat folded configuration, the protective article 100 lies substantially flat with the shield lower edge 116 overlapping the front of the mask central portion 126, thereby facilitating storage and packaging.

When the protective article 100 is opened into a ready-to-use configuration, as shown in FIG. 3, the shield lower edge 116 continues to overlap the front of the mask central portion 126. In this first position, the shield 110 extends upward from the mask central portion 126 in a substantially rigid manner, at substantially the same angle as the mask central portion 126. The shield 110 curves creaselessly, following the curve of the mask 120. When the mask 120 is placed over a wearer's nose and mouth, and is attached to the wearer's head by an attachment means, such as elastic head bands 132 and 134, or ear loops (not shown), the shield 110 protects the portions of the wearer's face not covered by the mask 120, as shown in FIG. 1. The shield 110 overlap of the mask central portion 126 keeps liquids from penetrating the protective article 100 by splattering up under the shield lower edge 116.

When the protective article 100 is in an open configuration, either ready-to-use or worn on a face, the shield 110 is adapted to move into a second position, as shown in FIG. 4. A portion of the shield lower edge 116 moves behind the mask central portion 126 causing the shield 110 to angle toward the wearer's face, still maintaining its substantially rigid and curved configuration. This second position is aided by providing projections 118 in the shield lower edge 116. The projections 118 engage the mask 120 behind the central portion upper edge 127, allowing the wearer to position and angle the shield 110 with respect to the wearer's face. Multiple projections 118 can be formed in the shield lower edge 116, thereby providing shield adjustability for optimum shield visibility and comfort. In the second position, the shield 110 engages both the mask upper portion 128 and the mask central portion 126, thereby keeping liquids from penetrating the protective article 100. The shield lower edge 116 may also be contoured to facilitate wearer fit.

Figure 6:
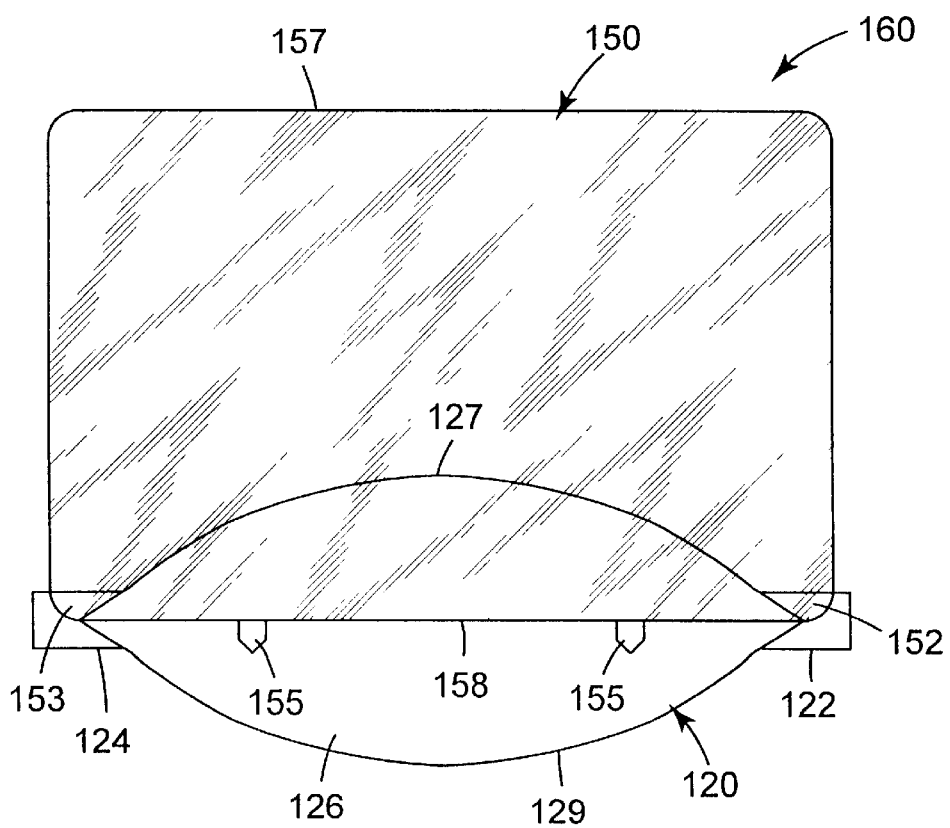
FIG. 6 is a front view of an alternate embodiment of a protective article.
Figure 7:
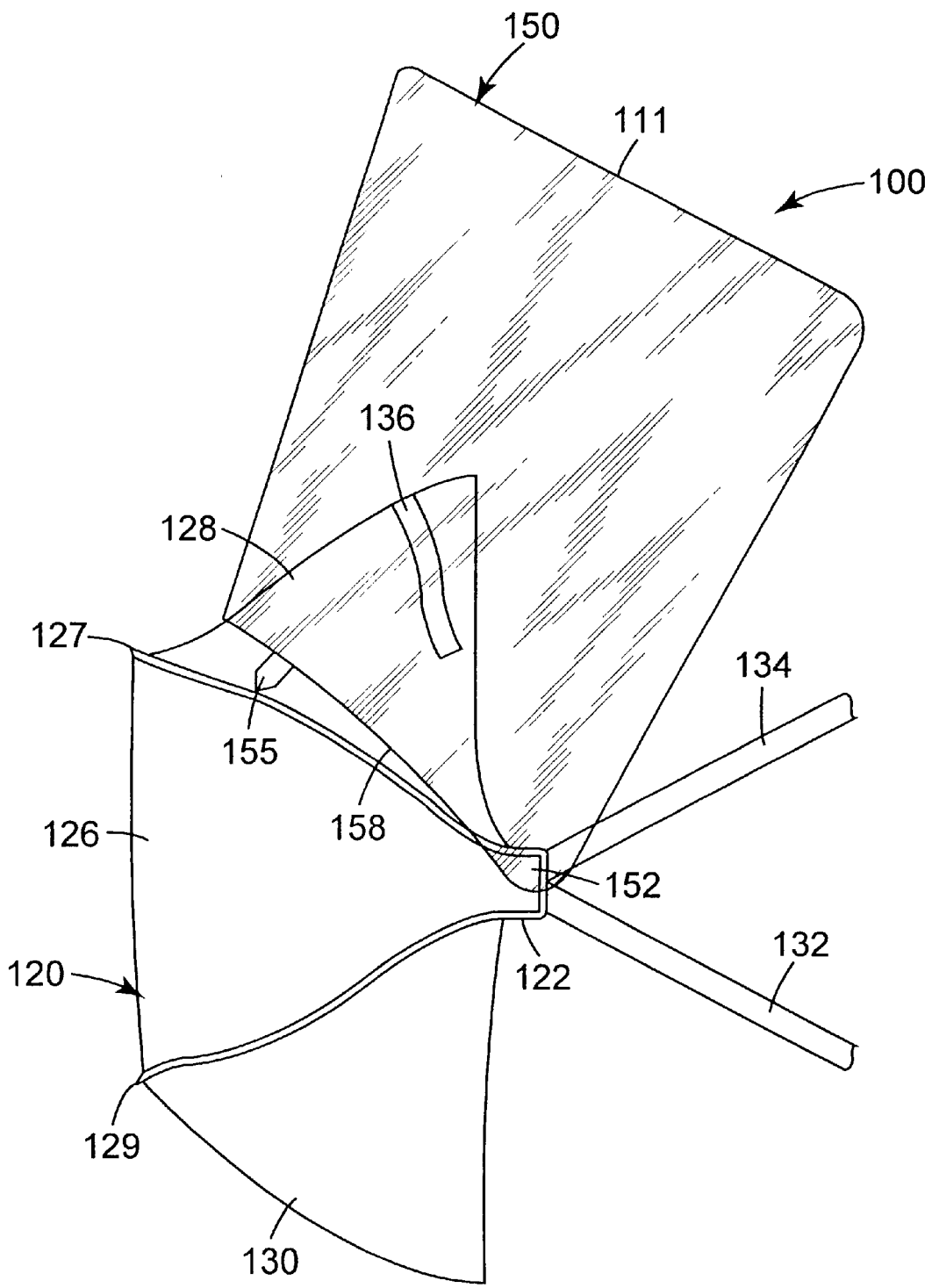
FIG. 7 is a side view of the protective article shown in FIG. 6.

An alternate embodiment of a protective article 160 is shown in FIGS. 6 and 7 having a differently configured shield 150 attached to mask 120. Shield 150 differs from shield 110 (shown in FIGS. 1–4) in that shield upper edge 157 and shield lower edge 158 are not arcuate. In addition, the shield lower edge projections 155 are flexible, pointed tabs projecting out from shield lower edge 158.

FIG. 6 is a front view of a protective article 160 in the flat folded configuration in which shield 150 is located in the first position. FIG. 7 is a side view of protective article 160 in the open, ready-to-use configuration, in which shield 150 is located in the second position. In this second position, the shield lower edge 158 and projections 155 are behind the mask central portion 126, resting on top of the mask upper portion 128. Projections 155 flex outward, away from the wearer's face (not shown), engaging the central portion upper edge 127, thereby securing the shield 150 in place with respect to the wearer's face. Although two projections 155 are shown, one or more may be used. In addition, the size, shape, and location of projections 155 may also vary, in order to secure and position the shield 150, as desired.

Shield 150 attaches near the lower, outer shield corners 152 and 153 to the mask 120 at the mask outer edges 122 and 124, in a manner similar to the first embodiment described above. All features of shield 150, such as materials and function, are the same as described for shield 110.

Figure 8A:
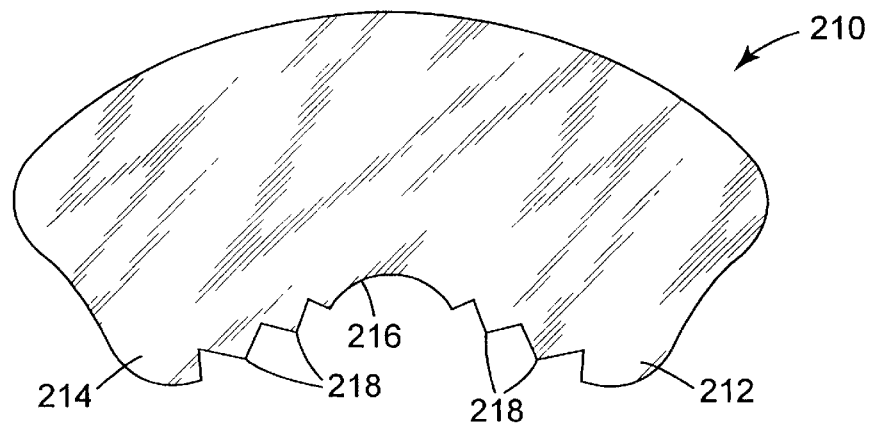
FIG. 8a is an alternate shield configuration with multiple lower edge projections.
Figure 8B:
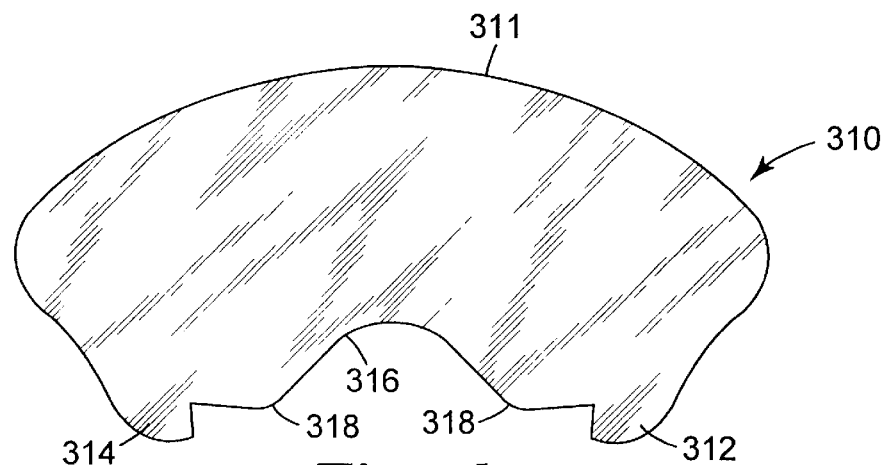
FIG. 8b is another alternate shield configuration with contoured lower edge projections.
Figure 8C:
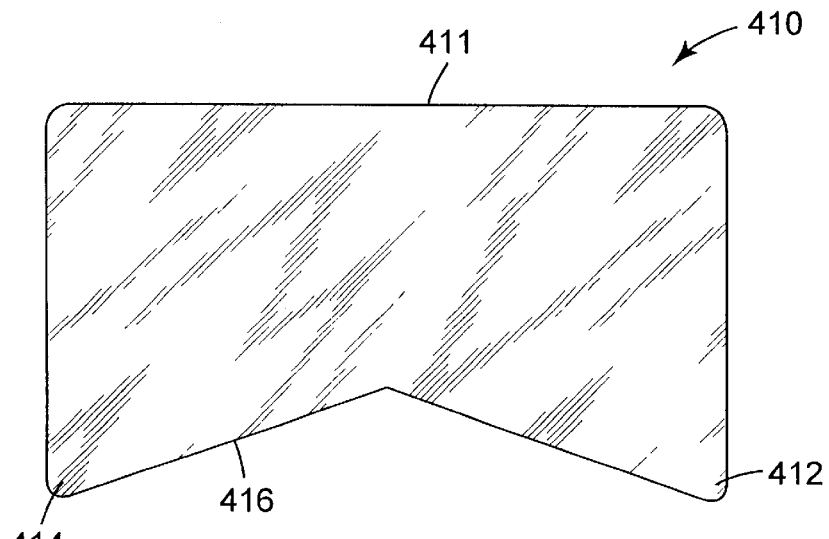
FIG. 8c is yet another alternate shield configuration without lower edge projections.

Additional alternate shield configurations are shown in FIGS. 8a, 8b and 8c. Shield 210, in FIG. 8a, includes a substantially arcuate lower edge 216 having multiple projections 218, and a substantially arcuate upper edge 211. The projections 218 are located between two outside corner attachment areas 212 and 214. These multiple projections 218 increase adjustability of the shield 210. Shield 310, in FIG. 8b, includes a contoured lower edge 316 having two projections 318, and a substantially arcuate upper edge 311. The projections 318 are located between two outside corner attachment areas 312 and 314. Shield 410, in FIG. 8c, includes an inverted 'V' shaped lower edge 416 with no projections, and a substantially flat upper edge 411. Two outside corner attachment areas 412 and 414 are also provided.

Numerous flat-fold mask designs may be combined with the above-described shield to form protective articles. For example, the mask may be provided in the form of a respirator. Examples of useful respirator designs are shown and described in a patent application entitled "Flat-Folded Personal Respiratory Protection Devices and Processes for Preparing Same," U.S. Ser. No. 08/612,527, assigned to the same assignee as the present application and hereby incorporated by reference.

The shape of the flat-fold mask may vary. Similarly, the shape of the upper and lower portions may vary. Each of the upper and lower portions must be shaped such that they can be joined to the central portion as previously described. The shape of any unattached edge portions of the upper and lower portions may also vary from straight to curvilinear, as desired, to achieve good fit to the wearer's face. Varying the shape of the joined portions can improve the fit of the respirator to the face.

The filter media incorporated in the mask or respirator for at least one of the upper, central, or lower portions may be formed from a number of woven and nonwoven materials. It may be in the form of a single or multi-layer construction, and may include an inner or outer cover layer or scrim. Examples of suitable filter materials include microfiber webs, fibrillated film webs, airlaid or carded staple fibers, solution-blown fiber webs, and combinations thereof.

The mask may also include a stiffening member. Preferably, the central portion is provided with a stiffening member.

Other embodiments are within the following claims.

What is claimed is:

1. A protective article comprising:
    (a) a mask comprising
        (i) a central portion having a pair of opposed edges,
        (ii) a first portion joined to an edge of the central portion,
        (iii) a second portion joined to the other edge of the central portion,
        at least one of the central, first and second portions being formed from filter media; and
    (b) a flexible, transparent shield having upper and lower edges, and dimensioned to cover the portion of the wearer's face not covered by the mask, the shield lower edge comprising at least one projection,
        the shield being attached to the mask and adapted to be moved between a first position in which the shield lower edge and lower edge projection lie in front of the mask central portion, and a second position in which the lower edge projection engages the mask such that at least a portion of the shield lower edge lies behind the central portion.

2. The protective article of claim 1, wherein the upper and lower edges of the shield are substantially arcuate.

3. The protective article of claim 1, wherein the shield lower edge comprises outside corners, and the shield is attached to the mask at the outside corners.

4. The protective article of claim 3, wherein the shield is removably attached to the mask at one of the outside corners.

5. The protective article of claim 4, wherein the lower edge of said shield comprises a centrally located, arcuately shaped cut-out portion intermediate a pair of projections.

6. The protective article of claim 3, wherein the shield is removably attached to the mask at both of the outside corners.

7. The protective article of claim 1, wherein the mask comprises a respirator.

8. The protective article of claim 1, wherein the shield lower edge comprises a plurality of projections.

9. The protective article of claim 1 further comprising a nose clip.

10. The protective article of claim 1, wherein said shield further comprises an anti-fogging, anti-reflective coating.

11. The protective article of claim 10, wherein said anti-fogging, antireflective coating comprises inorganic metal oxide particles.

12. The protective article of claim 1, wherein the shield is adapted to attach to a wearer's head.

13. The protective article of claim 1, wherein the shield further comprises an anti-glare strip.

14. The protective article of claim 1, wherein said mask further comprises an anti-glare strip.

15. A protective article comprising:
    (a) a mask comprising
        (i) a central portion having a pair of opposed edges,
        (ii) a first portion joined to an edge of the central portion,
        (iii) a second portion joined to the other edge of the central portion,
        at least one of the central, first and second portions being formed from filter media; and
    (b) a flexible, transparent shield having upper and lower edges, and dimensioned to cover the portion of the wearer's face not covered by the mask,
        the shield being attached to the mask and adapted to be moved between a first position in which the shield lower edge lies in front of the mask central portion, and a second position in which at least a portion of the shield lower edge lies behind the central portion.

* * * * *